United States Patent
Lin et al.

(10) Patent No.: US 10,413,248 B2
(45) Date of Patent: Sep. 17, 2019

(54) NON-CONTACT METHOD FOR DETECTING PHYSIOLOGICAL SIGNAL AND MOTION IN REAL TIME

(71) Applicant: NATIONAL TAIWAN UNIVERSITY OF SCIENCE AND TECHNOLOGY, Taipei (TW)

(72) Inventors: Yuan-Hsiang Lin, Taipei (TW); Yu-Chen Lin, Taipei (TW); Guan-You Lin, Taipei (TW); Meng-Han Li, Taipei (TW)

(73) Assignee: NATIONAL TAIWAN UNIVERSITY OF SCIENCE AND TECHNOLOGY, Taipei (TW)

( * ) Notice: Subject to any disclaimer, the term of this patent is extended or adjusted under 35 U.S.C. 154(b) by 666 days.

(21) Appl. No.: 15/193,196

(22) Filed: Jun. 27, 2016

(65) Prior Publication Data

US 2017/0007185 A1    Jan. 12, 2017

(30) Foreign Application Priority Data

Jul. 9, 2015    (TW) .............................. 104122281 A (51) Int. Cl.
*A61B 5/00*    (2006.01)
*A61B 5/11*    (2006.01)
*A61B 5/103*    (2006.01)
*A61B 5/024*    (2006.01)

(52) U.S. Cl.
CPC .......... *A61B 5/721* (2013.01); *A61B 5/02433* (2013.01); *A61B 5/1032* (2013.01); *A61B 5/1121* (2013.01); *A61B 5/1128* (2013.01); *A61B 5/7278* (2013.01); *A61B 5/746* (2013.01); *A61B 2562/0233* (2013.01)

(58) Field of Classification Search
CPC ............................................. G06T 2207/30076
See application file for complete search history.

(56) References Cited

U.S. PATENT DOCUMENTS

| | | | | |
|---|---|---|---|---|
| 8,295,567 B2* | 10/2012 | Watson | ................. | A61B 5/0816 381/94.1 |
| 8,855,384 B2* | 10/2014 | Kyal | .................... | G06K 9/0057 382/107 |
| 2010/0067739 A1* | 3/2010 | Mostafavi | ............... | G06T 7/285 382/103 |

(Continued)

*Primary Examiner* — Gandhi Thirugnanam
(74) *Attorney, Agent, or Firm* — Bacon & Thomas, PLLC (57) ABSTRACT

A method includes: sensing a portion of a human body to generate a series of image frames by an optical sensing element; determining a complexion region from each of the image frames; then calculating a central coordinate of the complexion region; determining a sample block by expanding a surrounding range from the central coordinate, for getting a complexion fluctuation waveform; comparing the central coordinate with a central coordinate of a later image frame, to calculate a displacement in a unit time for determining whether the portion of the human body is in a static state. In the static state, an operating unit performs noise filter and peak detecting for complexion fluctuation waveform, and calculates a physiological signal. The method can reduce the amount of data required to be processed in physiological signal detection, and improve the accuracy of the detection.

10 Claims, 7 Drawing Sheets

(56) References Cited

U.S. PATENT DOCUMENTS

| | | | | |
|---|---|---|---|---|
| 2013/0342670 A1* | 12/2013 | Kyal | .................... | A61B 5/7225 |
| | | | | 348/77 |
| 2014/0072190 A1* | 3/2014 | Wu | ........................ | G06T 7/262 |
| | | | | 382/128 |
| 2014/0276099 A1* | 9/2014 | Kirenko | ................ | G06T 7/0016 |
| | | | | 600/476 |
| 2015/0262338 A1* | 9/2015 | Xu | ........................... | G06T 7/20 |
| | | | | 382/128 |
| 2015/0332457 A1* | 11/2015 | Mestha | ............. | G06K 9/00362 |
| | | | | 382/103 |
| 2015/0379370 A1* | 12/2015 | Clifton | ................ | A61B 5/0205 |
| | | | | 382/128 |
| 2016/0235312 A1* | 8/2016 | Jeanne | ..................... | A61B 5/72 |
| 2016/0374605 A1* | 12/2016 | Pandian | .............. | A61B 5/0205 |
| | | | | 600/323 |
| 2017/0007185 A1* | 1/2017 | Lin | ........................ | A61B 5/721 |
| 2017/0039702 A1* | 2/2017 | Wang | ..................... | G06T 7/0012 |
| 2017/0340289 A1* | 11/2017 | Lin | ........................ | A61B 5/024 |
| 2017/0367580 A1* | 12/2017 | DiMaio | ............... | A61B 5/0064 |
| 2019/0082972 A1* | 3/2019 | Tao | ..................... | A61B 5/1102 |

\* cited by examiner

NON-CONTACT METHOD FOR DETECTING PHYSIOLOGICAL SIGNAL AND MOTION IN REAL TIME

BACKGROUND OF THE INVENTION (1) Field of the Invention

The present invention relates to a physiological signal detection method, particularly for one of non-contact method for detecting physiological signal and motion in real time.

(2) Description of the Prior Art

Following with the progress of the times, people pay more attention to the daily life of self-health management so that the real-time detection of various physiological signals to assess the physiological state becomes prerequisite, in which the heart rate is one of important health indicators. Currently heart rate detecting methods can be divided into two categories of contact and non-contact detecting methods. For contact detecting method, it is performed in vitro mode with adhesive electrode pad(s) or detecting device(s) worn on the human body to be detected. For non-contact detecting method, it is normally based on the camera to capture images of the human body to analyze volumetric measurement of a blood vessel for optically obtaining a plethysmogram, which is referred as photoplethysmogram (PPG).

Generally speaking, the contact detecting method requires a lot of medical supplies such as pads, disinfection appliances. In addition to the issues caused by cumbersome pasting process of electrode pad or wound wire, there are also some problems such as susceptible to allergic reactions to infection caused by exposure, especially for baby due to more delicate skin. Therefore, the contact detecting method is neither suitable for long-term clinical monitoring nor applying to the wound skin.

Conversely, comparing to the contact detecting method, the non-contact detecting method does not have these problems aforesaid. However, for non-contact detecting method, the photoplethysmogram (PPG) is more susceptible to minor fluctuation incurred by external noise such as movement of body and change of ambient light sources so that the photoplethysmogram (PPG) is difficult to accurately interpret signal(s) in analysis and calculation.

In view of this dilemma issue abovementioned, the non-contact physiological signal detecting system with features in reducing the quantity of processing data/information and enhancing the accuracy of physiological signal(s) detection becomes the future trend in research and development field.

SUMMARY OF THE INVENTION

The object of the present invention is to provide a non-contact method for detecting physiological signal and motion in real time features in not only reducing quantity of operating data/information but also enhancing stability and accuracy in detecting physiological signal(s).

In order to achieve the object aforesaid, the present invention provides a non-contact method for detecting physiological signal and motion in real time, comprising steps of: sensing a portion of a human body to generate a first image frame and a second image frame by an optical sensing element, wherein the second image frame is generated later than the first image frame; providing a complexion judging mechanism by an operating unit for determining a first complexion region from the first image frame, and the operating unit calculating a first central coordinate of the first complexion region; determining a first sampling block by acquiring a specific surrounding range expanded with the first central coordinate as an expanding center; determining a second complexion region from the second image frame by executing the complexion judging mechanism, and calculating a second central coordinate of the second complexion region; determining a second sampling block by acquiring another specific surrounding range expanded with the second central coordinate as another expanding center; comparing the first central coordinate with the second central coordinate, to calculate a displacement in a unit time; discriminating whether a motion state of the portion of the human body is in a static state according to the displacement; the operating unit calculating a physiological signal formed as a complexion fluctuation waveform in accordance with a complexion fluctuation between the first sampling block and the second sampling block if the motion state of the portion of the human body is in the static state; and transmitting the physiological signal to a relevant receiving device.

In an embodiment, said non-contact method further comprises steps of: the operating unit calculating an area of the first complexion region; judging whether the area of the first complexion region is larger than a preset area or not; and displaying the first sampling block in a succeeding image frame following the first image frame on a display unit, and the operating unit determining the portion of the human body is really sensed by the optical sensing element if the area of the first complexion region is larger than a preset area threshold. However, if the area of the first complexion region is smaller than the preset area threshold, the operating unit will generate and send a warning signal to the relevant receiving device to alert a user.

In an embodiment, said non-contact method further comprises steps of: the operating unit executing a motion detecting mechanism comprising steps of: receiving a first displacement critical value and a second displacement critical value preset by an user, wherein the first displacement critical value is less than the second displacement critical value; the operating unit retrieving the first displacement critical value and the second displacement critical value to respectively compare with the displacement; if the displacement is not greater than the first displacement critical value, then the operating unit defining the portion of the human body is in a static state; if the displacement is greater than the first displacement critical value and not greater than the second displacement critical value, then defining the portion of the human body is in a slightly motion state; if the displacement is greater than the second displacement critical value, then defining the portion of the human body is in a violent motion state; and changing the first displacement critical value and the second displacement critical value by the operating unit, to adjust a sensitivity of the motion detecting mechanism.

In an embodiment of said non-contact method, each of the first image frame and the second image frame includes a plurality of pixels, the operating unit executes the complexion judging mechanism to judge that each of the pixels is a skin-color pixel or a nonskin-color pixel, wherein the complexion judging mechanism comprises steps of: selecting one of the pixels to be a central pixel, and defining a judging block by outspreading from the central pixel to the surrounding thereof; calculate an area ratio of a skin-color area located in the judging block to an entire area of the judging block, wherein the skin-color area is formed by the skin-color pixels in the judging block and located around the central pixel; the operating unit receiving a reference ratio preset by the user, and comparing the area ratio with the reference ratio; and determining the central pixel is a non-skin-color pixel if the area ratio is less than the reference ratio.

In an embodiment, said non-contact method further comprises: the operating unit calculating one of an average of red channel signals, an average of green channel signals and an average of blue channel signals for each of the first sampling block and the second sampling block, to create a complexion fluctuation waveform, which will be used in succeeding processes of motion range detection.

In an embodiment, said non-contact method further comprises: obtaining a real ambient illuminance via the optical sensing element; the operating unit receiving an illuminance threshold preset by the user, and comparing the real ambient illuminance with the illuminance threshold by the operating unit, so as to obtain a comparing result; preparing a light source of infra-red, and selecting one of a switch-on mode and a switch-off mode for the light source of infra-red in accordance with the comparing result; switching the light source of infra-red into the switch-off mode and using the average of green channel signals for creating the complexion fluctuation waveform if the real ambient illuminance is greater than the illuminance threshold as the comparing result; and switching the light source of infra-red into the switch-on mode and using the average of red channel signals for creating the complexion fluctuation waveform if the real ambient illuminance is less than the illuminance threshold as the comparing result.

In an embodiment, said non-contact method further comprises: inputting the physiological signal into an infinite impulse response filter to perform filtering process for generating an output signal; subsequently, providing a moving average algorithm for the operating unit; the operating unit executing the moving average algorithm to smooth a waveform of the output signal generated from the infinite impulse response filter, and eliminate high-frequency noises. Overall, the infinite impulse response filter cooperated with the moving average algorithm can reduce the noises caused by movement during measurement, respiration, unconsciously shaking and slight ambient lighting fluctuation.

In forgoing embodiments, the operating unit is a field-programmable gate array with an internal microprocessor, the field-programmable gate array executes the complexion judging mechanism, and the internal microprocessor calculates the physiological signal.

In summary all foregoing exemplary embodiments of the present invention, the non-contact method for detecting physiological signal and motion in real time abovementioned features following innovational contrivances: a determining mechanism for detecting human body for determining whether the human body is detected; a motion detecting mechanism is executed before the calculation of physiological signal according to the complexion signals of the portion of the human body, to determine motion range for discriminating different motion states; and a complexion judging mechanism for determining whether the pixel in the image frame of the sensed portion of the human body is complexion or non-complexion. Accordingly, only in the static state, the complexion fluctuation waveform is adopted by the operating unit to perform succeeding processes such as noise filtering, peak detecting and calculation of physiological parameter value such as heartbeat value. However, in the slightly motion state and the violent motion state, the operating unit does not take current waveform sections to process succeeding process(es) to calculate the physiological parameter value until next static state happens. Therefore, said method not only reduces the data or information to be processed in the whole detecting processes of physiological signal, but also improves the accuracy of detecting the physiological signal in the non-contact detection methodology.

DESCRIPTION OF THE PREFERRED EMBODIMENTS

Regarding technical contents, features and effects disclosed above and other technical contents, features and effects of the present invention will be clearly presented and manifested in the following detailed description of the exemplary preferred embodiments with reference to the accompanying drawings which form a part hereof. It is to be understood that other embodiments may be utilized and structural changes may be made without departing from the scope of the present invention. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless limited otherwise, the terms "connected," and "coupled," and variations thereof herein are used broadly and encompass direct and indirect connections, couplings, and mountings.

Figure 1:
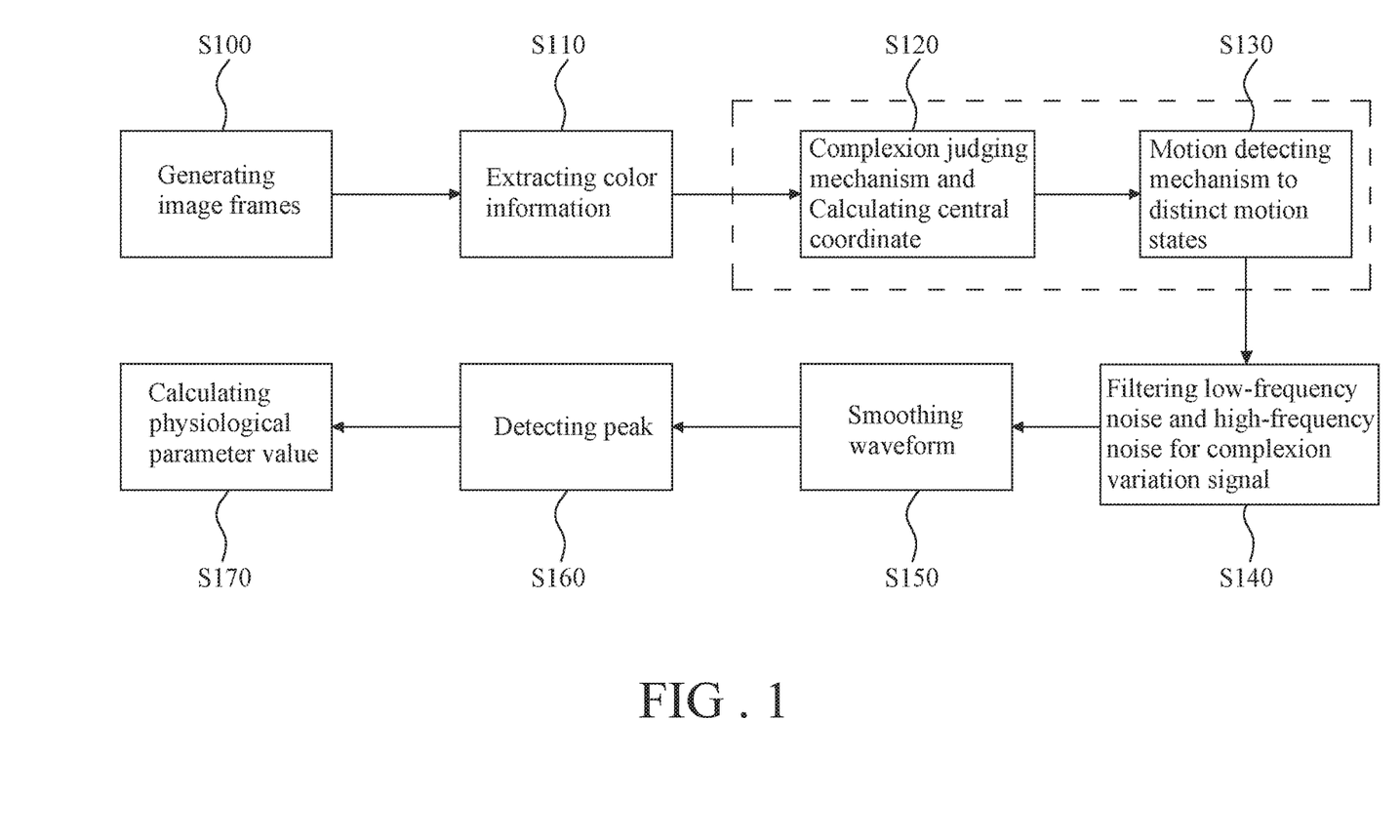
FIG. 1 is a block flowchart showing a general process of a non-contact method for detecting physiological signal and motion in real time for an exemplary embodiment of the present invention.

Please refer to FIG. 1, which is a block flowchart showing the general process of non-contact method for detecting physiological signal and motion in real time for an exemplary embodiment of the present invention. Firstly, by means of an optical sensing element, a portion of the human body is sensed for generating a series of image frames such that the series of image frames include a preceding first image frame and a succeeding second image frame (as shown in step S100). Both of the preceding first image frame and the succeeding second image frame are probably continuous or discontinuous discrete image frames, and the time interval between the preceding first image frame and the succeeding second image frame is arbitrarily set in accordance with the requirement of the practical operation. The captured image frames are screened for extracting color information after a process of exposure correction to record processes of complexion fluctuation and skin vibration/motion (as shown in step S110). Subsequently, by means of a complexion judging mechanism provided by an operating unit, the extracted color information of each of the image frames is processed for retaining a complexion region with an associated sampling block, and calculating the corresponding central coordinate of the complexion region so that the correlating position of the sampling block in the complexion region is also defined by the relevant central coordinate (as shown in step S120). Accordingly, a first central coordinate is calculated from the first image frame and a position of the first sampling block is also defined by the corresponding first central coordinate. A second central coordinate is calculated from the second image frame and a position of the second sampling block is also defined by the corresponding second central coordinate. Thereby, a corresponding displacement in a unit time is calculated out via comparing respective positions of the first and second central coordinates such that the displacement in a unit time is namely defined as the quantitative change of corresponding coordinates in a unit time. Finally, distinct motion states such as static state (namely rest), slightly motion state (namely flick or agitation) or violent motion state (namely jog) for the portion of the human body is discriminated via judging different motion ranges in accordance with the displacement calculated (as shown in step S130). If the motion state for the portion of the human body is in the static state, a physiological signal such as a heart-rate signal is calculated out to form an available waveform in accordance with the complexion fluctuation or complexion variation between the first and second sampling blocks from the corresponding first and second image frames. Based on the available waveform of the physiological signal, a physiological parameter value such as a heartbeat value is calculated out by the operating unit and displayed by a display unit.

In an exemplary embodiment of the present invention, the physiological signal abovementioned is created by physiological phenomena such as heart rate, which will cause change of complexion. In order to convert a complexion fluctuation signal or a complexion variation signal with numerous noise caused by movement during measurement, respiration, unconsciously shaking and slight ambient lighting fluctuation into a feasibly precise physiological signal, all low-frequency noise below 0.8 Hz and high-frequency noise above 3.4 Hz in foresaid complexion fluctuation signal or complexion variation signal is filtered out by means of an infinite impulse response (IIR) filter to output a transitional signal with frequency in range of 0.8 to 3.4 Hz for enhancing the accuracy of the real-time operation instantly (as shown in step S140). However, if a peak detecting procedure is directly applied to the transitional signal output from the infinite impulse response filter, which will result in erratic detection owing to the waveform of the transitional signal is susceptible to some high-frequency noises. Accordingly, the high-frequency noise in foresaid transitional signal is further eliminated out by means of a moving average algorithm (MA) for obtaining a desired final physiological signal with a smoothed waveform (as shown in step S150). Moreover, each peak is figured out by calculating each corresponding slope or gradient of the smoothed waveform at each time point (as shown in step S160). The physiological parameter value is calculated out via detecting each time point corresponding to the peak of the smoothed waveform (as shown in step S170).

In the foregoing exemplary embodiment of the present invention, any image input device such as camera or lens is possibly used as an optical sensing element. Any microprocessor-based device such as Field-programmable gate array (FPGA) with an internal microprocessor is possibly used as an operating unit. The optical sensing element and the operating unit are integrated into a built-in physiological signal detecting system (hereinafter referred to detecting system) to achieve the method aforesaid. The field-programmable gate array is employed to execute the complexion judging mechanism. The internal microprocessor serves as a physiological signal processor to calculate foregoing physiological signals or physiological parameter value. Noticeably, in order to improve the processing and operative effectiveness of physiological signal as well as to increase the stability and accuracy of the detecting system, in the present exemplary embodiment, a motion detection mechanism is inserted prior to the calculation of the final physiological parameter value (S170) for detecting the motion range for the portion of the human body (S130) so that the measurement accuracy is effectively promoted in consequence of reducing signal interference incurred by the movement of the human body. FIG. 1 is a block flowchart for the detecting system judging that the motion state for target portion of the human body is in static state. However, if recent motion state detected by the detecting system determines that the portion of the human body is in restless status of slightly motion state or violent motion state, the calculation of current heartbeat value should not be implemented, and the preceding heartbeat value in the last static state should be retained, and the detecting system should only transmit a judging result in current restless status to a mobile device such as Bluetooth module.

Figure 2:
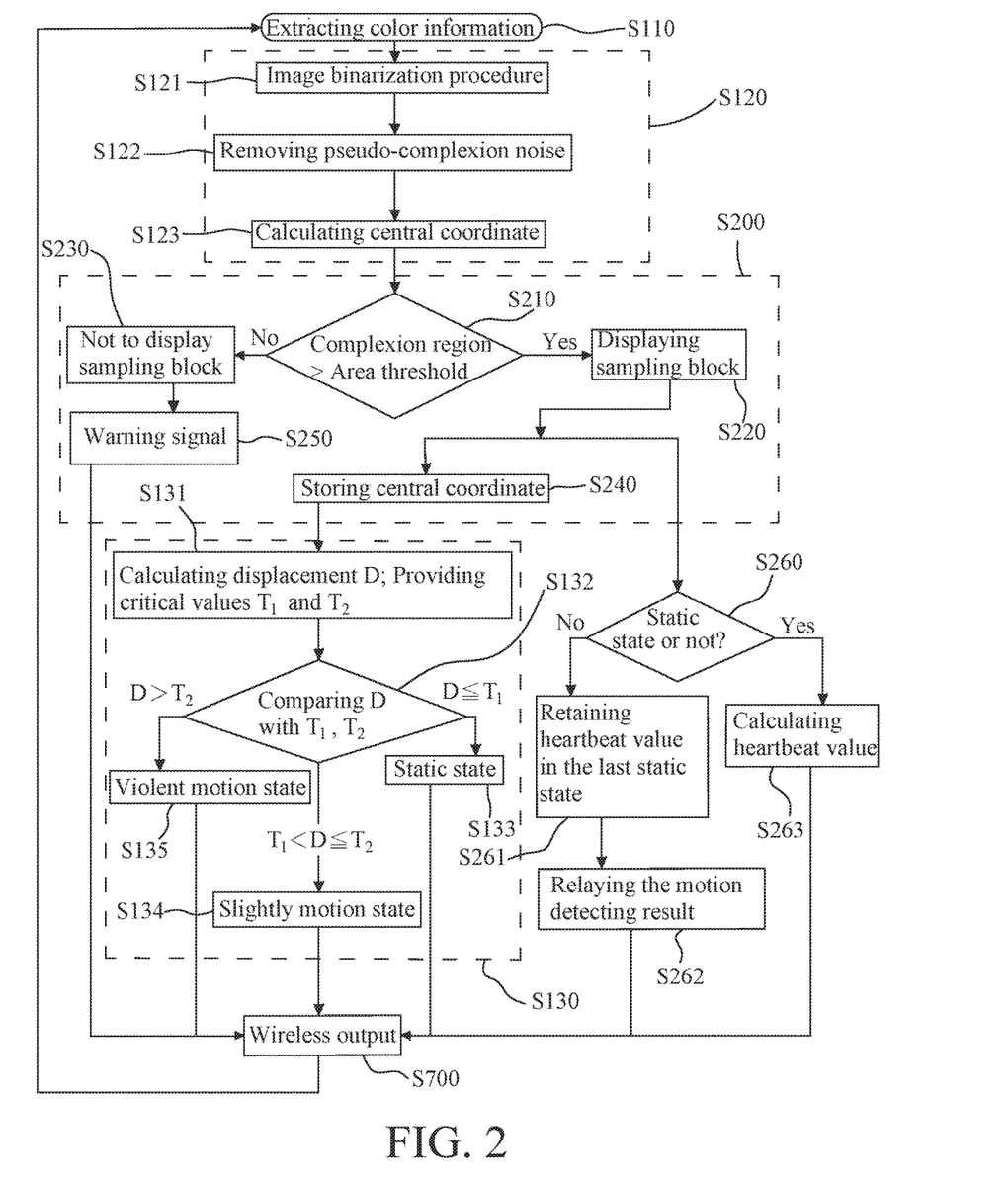
FIG. 2 is a schematic flowchart for a motion detecting mechanism in an exemplary embodiment of the present invention.

Please refer to FIGS. 1 and 2. In the present exemplary embodiment of the present invention, the process of the complexion judging mechanism described in previous step S120 is further disclosed here with preceding S110. The color information extracted from target image frames (S110) is retrieved for being processed with the complexion judging mechanism in present step S120. The complexion judging mechanism includes an image binarization procedure in S121 and a removal procedure of pseudo-complexion noise in S122. For the step S121, the pixels in the image frame are classified into a complexion category and a non-complexion category by an image binarization process. For the step S122, certain negative factor particular for a pseudo-complexion noise is taken into account that the pseudo-complexion noise means certain noise caused by a pseudo-complexion article or ambient luminance. In S122, the pixels in the image frame, which are sorted into the complexion category and features dispersed and small area, are filtered out via the removal procedure of pseudo-complexion noise. The complexion region in the image frame, which is formed by the pixels sorted into the complexion category and arranged in manner of continuous and large-area, are retained. Therefore, all pseudo-complexion noises are effectively removed. In S123, each central coordinate for the previous retained complexion region is calculated accordingly.

As shown in FIG. 2, in an exemplary embodiment of the present invention, a step S200 is inserted between the step S120 and step S130, which are previously described in association with foregoing FIG. 1 for determining whether the certain portion of the human body is really sensed by the optical sensing element. The process of step S200 is performed by following procedure. Firstly, calculate an area of the previous retained complexion region, which is reserved from sub-step S122 in the step S120 of the complexion judging mechanism. The area of complexion region is exemplarily as the sum of the number of pixels encompassed by the complexion region. Subsequently, compare the area of the complexion region with a preset area threshold for determining whether the certain portion of the human body is really sensed by the optical sensing element so that the comparing results are divided into following two sets of set-A (step S220) and set-B (step S230). An exemplary area threshold is arbitrarily defined as specific number of pixels for serving as judging standard here (as shown in step S210). Set-A is that the certain portion of the human body is really sensed by the optical sensing element if the area of the complexion region is greater than the preset area threshold (as shown in step S220). In set-A, the succeeding image frame following the current image frame is necessary to display the sampling block so that the procedural step S220 is bifurcated into sub-steps S240 and S260, where the sub-step S260 is further branched into subsidiary step S263 as well as subsidiary serial steps S261 and S262. The sampling block is defined by acquiring a specific surrounding range expanded from the central coordinate as an expanding center to the surrounding of the central coordinate in the complexion region. An exemplary sampling block is defined as a matrix of 50×50 pixels. Set-B is that the certain portion of the human body is not really sensed by the optical sensing element if the area of the complexion region is smaller than the preset area threshold (as shown in step S230). In set-B, the succeeding image frame following the current image frame is not necessary to display sampling block so that the procedural step S230 is jumped into sub-step S250 for functioning as anti-asphyxia detection after related procedure of the step S230 has been finished. Finally, all different ranked steps including S240, S250, S262 and S263 are merged into ending step S700 with step S240 is by way of general step S130 (as shown in FIG. 2).

When the certain portion of the human body is not really sensed by the optical sensing element, the detecting system functions as an anti-asphyxia detecting system by offering a warning signal generated from the operating unit to cell phone(s) related with warning indication of perceptible vibration, audible ring and visible short message in step S250. When the physiological signal detecting system is unable to sense an adequate complexion region from the image of infant face captured by the optical sensing element such as camera or lens, some circumstances may be clinically determined as that the face of the infant is covered by some undesired foreign object or the infant sleeps in face-down (namely prone decubitus in medical term) sleeping position. Aforementioned circumstances may cause the infant to be suffered from asphyxia, which should be immediately treated to avoid worsening circumstance incurred. In these circumstances, the physiological signal detecting system of the present invention is promptly able to send a warning signal generated from the operating unit to relevant receiving device(s) to alert related people.

If the certain portion of the human body is really sensed by the optical sensing element, then the procedural step S220 is bifurcated into sub-steps S240 and S260, where the sub-step S260 is further branched into subsidiary step S263 as well as subsidiary serial steps S261 and S262 after related procedure of the step S230 has been finished. In step S240, the comparing result reflects that certain portion of the human body is judged as really sensed so that the detecting system performs a coordinate staging once every 0.25 seconds, to store the central coordinate of the current sampling block in a register. In the exemplary embodiment of the present invention, there are two registers such that one register serves for temporarily storing a current central coordinate while the other register serves for temporarily storing a preceding central coordinate. The current central coordinate is shifted from one register to the other register once every 0.25 seconds. Once every 0.50 seconds, one after another central coordinates stored in two registers are retrieved to compare each other so that displacement in 0.25 seconds between one after another central coordinates is calculated, which will be used in the sub-step S131 of general step S130. On the other hand, at the same time during processing a new motion detection, the detecting system determines whether succeeding procedures of a heart-rate signal treatment and a heartbeat value calculation should be proceeded in accordance with recent motion state detected in step S260. If recent motion state detected is in the static status, the procedure jumps to subsidiary step S263 to perform a heart-rate detecting algorithm including noise-filtering via the infinite impulse response filter, waveform-smoothing via a moving average algorithm, the peak detecting and the heartbeat value calculating for the waveform of the complexion fluctuation signal or the complexion variation signal generated by the complexion judging mechanism treating each of the image frames input into the detecting system. If recent motion condition detected is not in the static state, the procedure jumps to subsidiary serial steps S261 and S262. For step S261, the detecting system retains preceding heartbeat value in the last static state. For step S262, the detecting system relays the motion detecting result such as slightly motion state or violent motion state to the Bluetooth module. In step S700, the motion detecting result are converted into wireless signals then output to related mobile devices.

Noticeably, as described in previous paragraph of step S130, the detecting system of the present invention is contrived to have motion detecting feature that it is able to determine motion range in order to distinguish different motion states in accordance with the displacement for the certain portion of the human body. For accomplishing aforesaid purpose, the exemplary embodiment of the present invention (as shown in FIG. 2) provides a motion detecting mechanism including sub-steps S131-S135 as below. In step S131, a preset first displacement critical value $T_1$ and a preset second displacement critical value $T_2$, together with a displacement D to be processed here are provided. The first displacement critical value $T_1$ is an adjustable lower limit of threshold parameter with arbitrary preset discretion. The second displacement critical value $T_2$ is also an adjustable upper limit of lintel parameter with arbitrary preset discretion such that the first displacement critical value $T_1$ is less than the second displacement critical value $T_2$. In step S132, the first displacement critical value $T_1$ and the second displacement critical value $T_2$ are retrieved to respectively compare with existing displacement D in accordance with following motion detecting rules. In step S133, if the displacement D is not greater than the first displacement critical value $T_1$ ($D \leq T_1$), the portion of the human body is define as in static state. In step S134, if the displacement D is greater than the first displacement critical value $T_1$ and not greater than the second displacement critical value $T_2$ ($T_2 \geq D > T_1$), the portion of the human body is defined as in slightly motion state. In step S135, if the displacement D is greater than the second displacement critical value $T_2$ (D>$T_2$), the portion of the human body is defined as in violent motion state. Since both of first displacement critical value T1 and second displacement critical value $T_2$ are adjustable parameters with arbitrary preset discretion, the sensitivity of the motion detecting mechanism is naturally adjustable by changing preset values for both of the first displacement critical value $T_1$ and second displacement critical value $T_2$.

In an exemplary embodiment of the present invention, previous system parameters are respectively defined. The displacement D denotes the linear distance between preceding central coordinate and succeeding central coordinate. The first displacement critical value $T_1$ denotes a spatial interval with two-pixel length. The second displacement critical value $T_2$ denotes a spatial interval with seven-pixel length. Accordingly, the motion detecting rules applied in previous paragraph is recapitulated as below. In step S133, if the linear distance between the preceding central coordinate and the succeeding central coordinate is not less than two-pixel length, the portion of the human body is defined as in static state. In step S134, if the linear distance between preceding central coordinate and succeeding central coordinate is greater than two-pixel length, but not greater than seven-pixel length, the portion of the human body is defined as in slightly motion state. And in step S135, if the linear distance between the preceding central coordinate and the succeeding central coordinate is greater than seven-pixel length, the portion of the human body is defined as in violent motion state.

In another exemplary embodiment of the present invention, previous system parameters are respectively defined. The displacement D denotes the combinational linear distance integrated by a horizontal displacement and a vertical displacement. The first displacement critical value $T_1$ denotes a spatial interval with one-pixel length. The second displacement critical value $T_2$ denotes a spatial interval with seven-pixel length. Similarly, the motion detecting rules applied in previous paragraph is recapitulated as below. In step S133, if the combinational linear distance integrated by a horizontal displacement and a vertical displacement is not less than one-pixel length, the portion of the human body is define as in static state. In step S134, if the combinational linear distance integrated by a horizontal displacement and a vertical displacement is greater than one-pixel length, but not greater than seven-pixel length, the portion of the human body is defined as in slightly motion state. And in step S135, if the combinational linear distance integrated by a horizontal displacement and a vertical displacement is greater than seven-pixel length, the portion of the human body is defined as in violent motion state.

Figure 3:
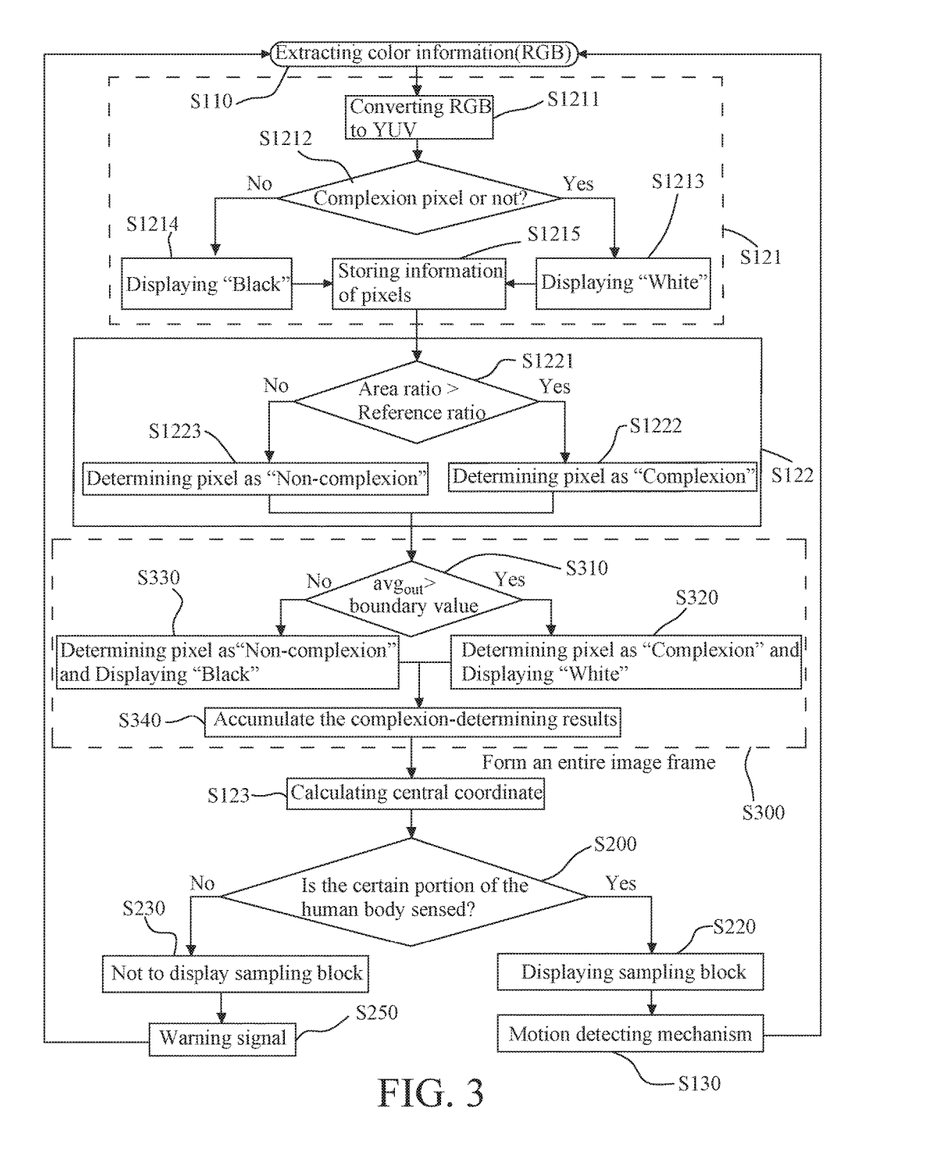
FIG. 3 is a schematic flowchart for a complexion judging mechanism with additional process of a temporal filtering mechanism (TF) for compensation of instant fluctuation in an exemplary embodiment of the present invention.

Please refer to FIGS. 2 and 3. FIG. 2 illustrates motion detecting mechanism. FIG. 3 illustrates further implement means with detailed procedure for steps S121 and S122 in FIG. 2 for an exemplary embodiment of the present invention. The implement means of step S121 is a kind of image binarization. The implement means of S122 is a kind of judging block. As described in previous paragraph for step S110, the color information extracted from target image frames is retrieved for being processed with the complexion judging mechanism in step S120. The color information is usually in format of RGB-channel signals (abbreviated as RGB-signals) derived from popular RGB-color model with symbol R denoting red color, symbol G denoting green color, and B symbol denoting blue color respectively. In step S1211, prior to further process of step S121, the RGB-signals are firstly converted into a format of YUV-color space (abbreviated as YUV-signals) via a conversion formula with symbol Y denoting luminance of color, symbol U denoting chrominance of color and V symbol denoting concentration of color respectively, wherein the conversion formula are shown as below:

$$Y = \frac{R + 2G + B}{4}$$

$$U = R - G$$

$$V = B - G$$

The U-signal (chrominance of color) and V-signal (concentration of color) in the YUV-color space for a specific pixel are applied in following exemplary judging conditions for determining whether the specific pixel is a complexion pixel (step S1212) after the RGB-signals have been converted into the YUV-signals, wherein exemplary judging conditions are shown as below:

$$10 < U < 74$$

$$-40 < V < 11$$

In step S1213, if the U-signal and V-signal for the specific pixel meet the exemplary judging condition aforesaid, the pixel is determined as complexion or as a skin-color pixel with following procedure: firstly, set each of R-channel signal, G-channel signal and B-channel signal into 10 bits "1"; then, display the pixel as "white" on a display unit such as a screen. In step S1214, if the U-signal and V-signal for the specific pixel does not meet the exemplary judging condition aforesaid, the pixel is determined as non-complexion or as a nonskin-color pixel with following procedure: firstly, set each of R-channel signal, G-channel signal and B-channel signal into 10 bits "0"; then, display the pixel as "black" on a screen. In step S1215, if the complexion judging procedure is completed, store all foregoing set complexion judging information related to all pixels referred in a register, whose storage capacity is sufficient for storing the information of all pixels of one image frame.

Figure 4:
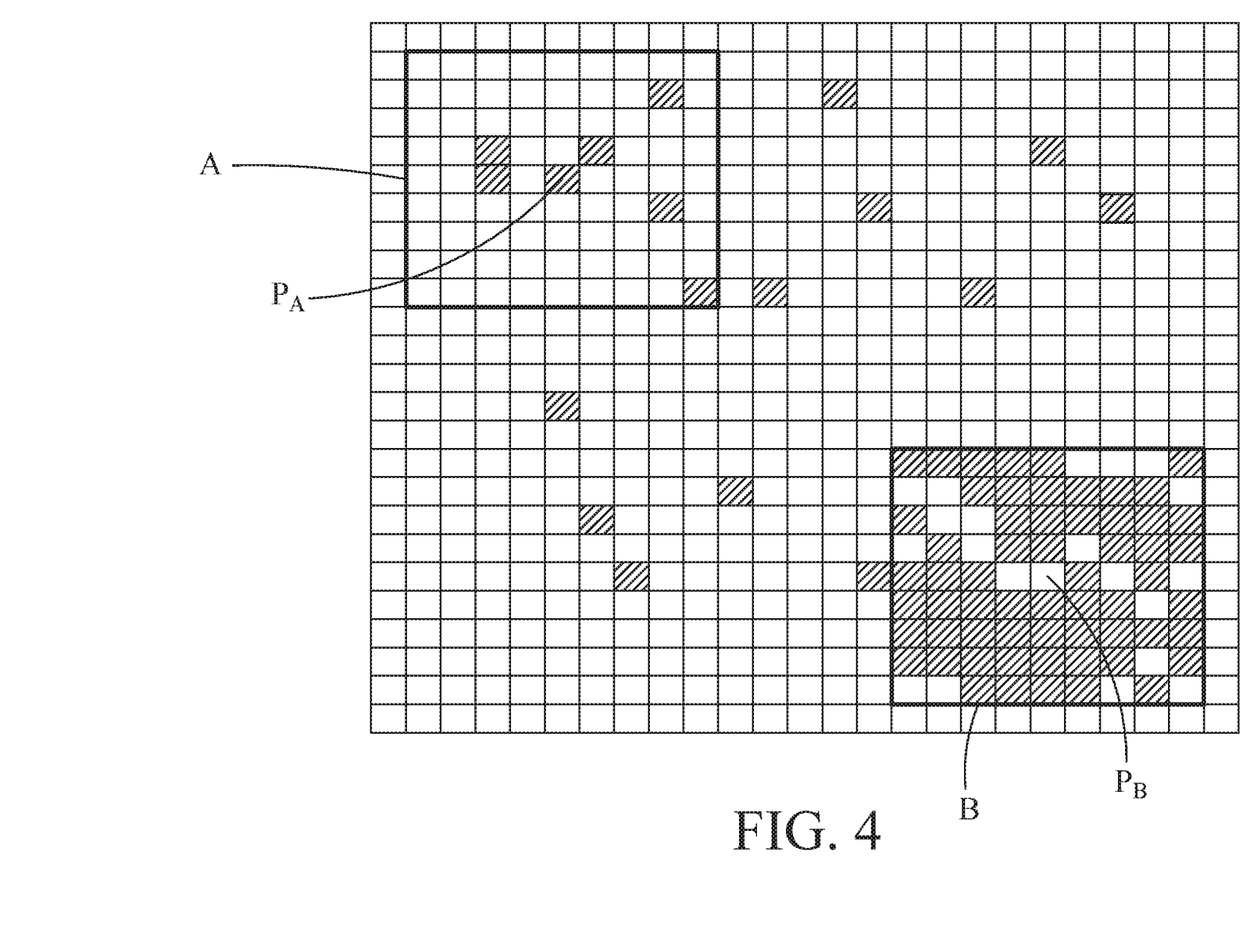
FIG. 4 is a schematic view showing the analyzing results in complexion judging mechanism for an exemplary embodiment of the present invention.

Please refer to FIG. 4, which is a schematic view showing the analyzing results in the complexion judgment mechanism for an exemplary embodiment of the present invention. In step S122, a central pixel is sampled to outspread with its surrounding to form a matrix of 9×9 as a judging block in the complexion judging mechanism. Calculate an area ratio of a skin-color area located in the judging block to an entire area of the judging block, wherein the skin-color area is formed by the skin-color pixels in the judging block and located around the central pixel. In an embodiment, preset a reference ratio which is exemplarily as 75% and features in arbitrary presetting discretion. The skin-color area is exemplarily as the number of the skin-color pixels encompassed by the judging block formed as a matrix of 9×9. The step S122 is further broken-down into following serial tertiary steps: in step S1221, comparing the area ratio with the reference ratio; in step S1222, if the area ratio is greater than the reference ratio (75%), the central pixel is determined as complexion; and in step S1223, if the area ratio is less than the reference ratio (75%), the central pixel is determined as non-complexion. For example:

The central pixel $P_A$: Although the central pixel $P_A$ is initially judged as complexion in accordance with the image binarization mechanism (step S121), however, the judge of the central pixel $P_A$ should be overridden as non-complexion in accordance with the removal procedure of pseudo-complexion noise (step S122) since the area ratio of the skin-color area in the judging block A and surrounding the central pixel $P_A$ to the overall area of the judging block A is less than the reference ratio (75%).

The central pixel $P_B$: Although the central pixel $P_B$ is initially judged as non-complexion in accordance with the image binarization mechanism (step S121), however, the judge of the central pixel $P_B$ should be overridden as complexion in accordance with the removal procedure of pseudo-complexion noise (step S122) since the area ratio of the skin-color area in the judging block B and surrounding the central pixel $P_B$ to the overall area of the judging block B is greater than the reference ratio (75%).

Accordingly, after executing image binarization mechanism (step S121), a lot of dispersed noise particles in the image frame will be eliminated, so leaving only the obvious skin-color area.

As shown in FIG. 3, in some circumstances for the exemplary embodiment of the present invention, the complexion judging result might become uncertainly unstable due to effect from the minor luminance fluctuation of ambient light source such as the flicker of the fluorescent light so that the step S300 for process of inserting a temporal filtering mechanism (TF) in compensation of instant fluctuation between existing steps S122 and S123 is necessary for reducing the uncertainty and instability of the complexion judging result incurred by the effect from the minor luminance fluctuation of ambient light source via following algorithm with associated formula, wherein the algorithm with associated formula is demonstrated as below:

$$avg_{out} = \left(\frac{3}{4}\right) avg_{in} + \left(\frac{1}{4}\right) data$$

Wherein, all variables therein are defined as below:

"data" denotes a color information for a pixel in current image frame, wherein the pixel does not be processed by the temporal filtering mechanism;

"$avg_{in}$" denotes a color information for a pixel in preceding image frame, wherein the pixel has been processed by the temporal filtering mechanism; and "$avg_{out}$" denotes a color information for a pixel in current image frame, wherein the pixel has been processed by the temporal filtering mechanism.

In step S310, a preset boundary value is provided for determining the color of a pixel to serve as criterion for comparing with current "$avg_{out}$" to determine whether the current color of the pixel is complexion. For example, the preset boundary value for determining the color of a pixel is arbitrarily set "0.06" in accordance with operational requirement. In step S320, if the current "$avg_{out}$" is not less than the "0.06", a complexion-determining result of the current color of the pixel is determined as complexion, and display the current color of pixel as "white" on a screen. In step S330, if the current "$avg_{out}$" is less than the "0.06", the complexion-determining-result of current color of the pixel is determined as non-complexion, and display the current color of the pixel as "black" on the screen.

In step S340, the transmitting mode in the exemplary embodiment of the present invention is serial transmitting mode instead of parallel transmitting mode. Therefore, in order to obtain an overall area for the complexion region of the entire image frame, the process of step S340 is performed to accumulate the complexion-determining results of all pixels existed in the entire image for obtaining a current overall result. The current overall result represents the overall area of the complexion region, and is defined the summation of the complexion-determining results for total color information of the pixels currently existed in the whole complexion region of the entire image frame encompassing the current color information of pixel. The current overall result is temporarily stored in a related field of a register, where the related field is specifically assigned for storing the value of the overall result. It also means the process for scanning the image frame is completed after the current overall result is obtained via foregoing accumulation. Subsequently, transmit the obtained overall result to the next step S123, where the current overall result is used for calculating out a corresponding central coordinate of the whole complexion region. Finally, the related field of the register is reset to zero after the current overall result has been transmitted to the next step S123.

Figure 5:
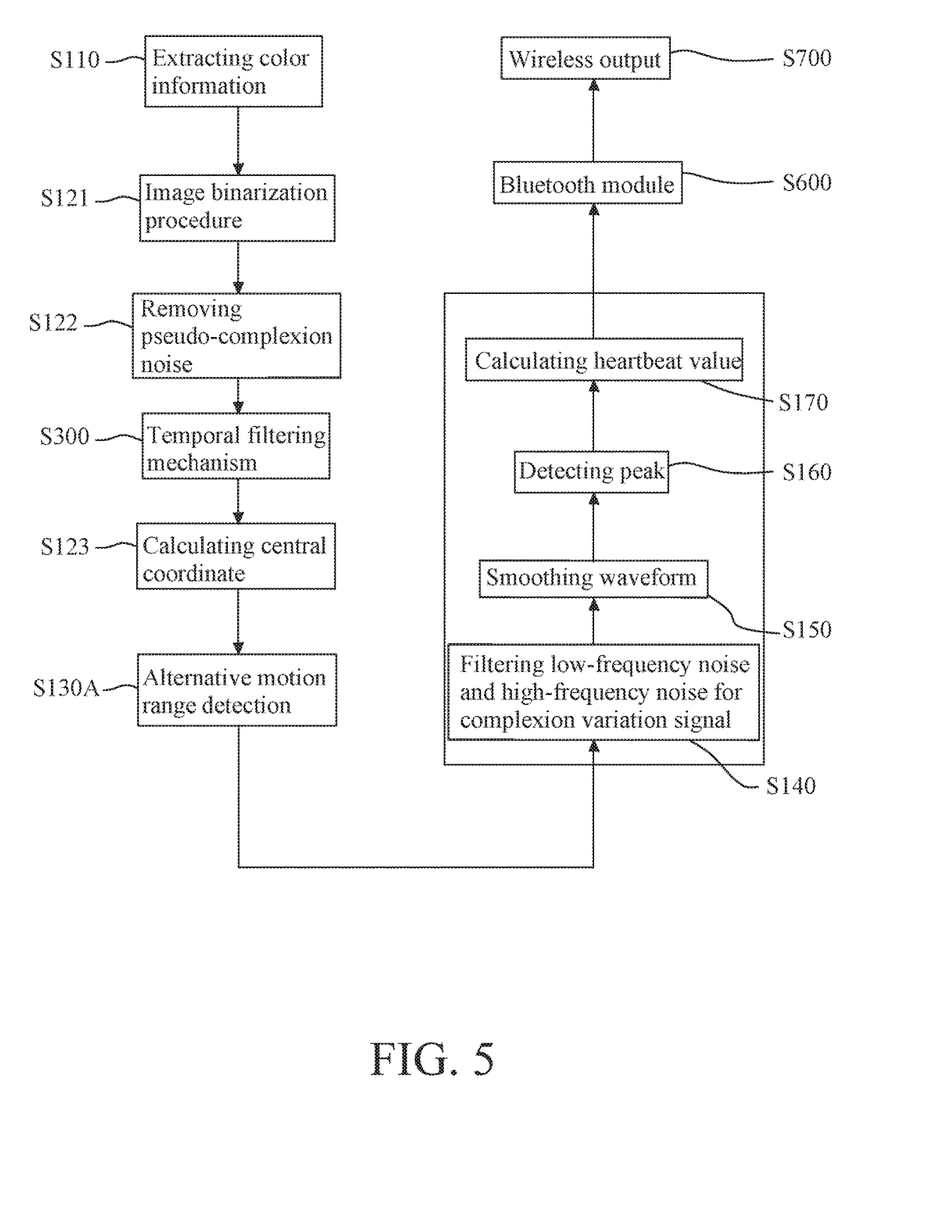
FIG. 5 is a schematic view showing the alternative method in using arithmetic means (colloquially average) of red, green or blue channel signals for determining motion range for another exemplary embodiment of the present invention.

Please refer to FIG. 5, which is a schematic view showing alternative method in using an arithmetic means (colloquially average) of red, green or blue channel signals for determining the motion range of the portion of the human body in another exemplary embodiment of the present invention. As shown in FIG. 5, the detecting system of the present invention adopts different adapted means for counterpart step S130A in contrast to primitive step 130 shown in FIG. 1 so that the corresponding overall block flowchart thereof is different from the combinational equivalent overall block flowchart of FIGS. 1 and 3 with primitive step 300 inserted between primitive steps 122 and 123 accordingly. Basing on this corresponding overall block flowchart with counterpart step S130A shown in FIG. 5, the corresponding overall process is stepwise described as below. In similar to primitive S100, by means of an optical sensing element, the certain portion of the human body is sensed for generating a series of image frames. In similar to primitive S110, the preceding image frames captured in step S100 are calculated via an operating unit to extract RGB color information after a process of exposure correction to record processes of complexion fluctuation and skin vibration/motion. In similar to primitive S120, by means of a complexion judging mechanism, the extracted RGB color information of the image frames are processed with the image binarization procedure in S121 and the removal procedure of pseudo-complexion noise in S122 for getting analyzing results of the complexion judgment mechanism, as well as additional process of the temporal filtering mechanism (TF) for compensation of instant fluctuation in inserted step S300 between existing steps S122 and S123. In similar to primitive S123, the central coordinate for each of previous retained pixels in the complexion region is calculated accordingly. In adapted step S130A, the process is modified as below: firstly, configure the retained pixel of the complexion region into a sampling block as matrix of 50×50 pixels arbitrarily; subsequently, create a luminance fluctuation waveform in complexion surface of the sampling block via calculation on the arithmetic means (colloquially average) for red channel signal, green channel signal or blue channel signal by an arithmetic multiplier; and finally, discriminate distinct motion range for the portion of the human body in accordance with the luminance fluctuation waveform in complexion surface of the sampling block above created. For other rest processing steps such as S140, S150, S160 and S170 in this corresponding overall block flowchart, they are all the same as those in corresponding primitive processing steps shown in FIG. 1.

In an exemplary embodiment, the detecting system of the present invention provides a night mode. The night mode is implemented by the optical sensing element and the operating unit therein such that an illuminance of ambient is sensed by the optical sensing element while the option of light source is determined by the operating unit with mechanism thereof as below. Firstly, prepare a light source of infra-red (IR), and preset an arbitrary illuminance threshold such as 140 illuminance lux unit in accordance with operational requirement, as well as obtain a real ambient illuminance via the optical sensing element. Subsequently, compare the ambient illuminance with the illuminance threshold. If the ambient illuminance is less than the illuminance threshold, then the light source of infra-red is switched on to function as a substituted light source, and the detecting method for the heart-rate signal is automatically regulated to adapt with alternative light source of infra-red. Accordingly, the channel signal for creating required complexion fluctuation waveform is changed from original arithmetic means (colloquially average) of the green channel signal into replacing arithmetic means of the red channel signal. If the ambient illuminance is greater than the illuminance threshold, then the light source of infra-red (IR) is switched off, and the detecting method for the heart-rate signal is remained. Accordingly, the channel signal for creating required complexion fluctuation waveform is not changed, where the original arithmetic means of the green channel signal is still applicable here. With foregoing mechanism thereof, the detecting system of the present invention is able to employ daylong for automatic switching and selecting different light sources and different color channel signals in accordance with the ambient illuminance to adapt with nighttime application.

Figure 6:
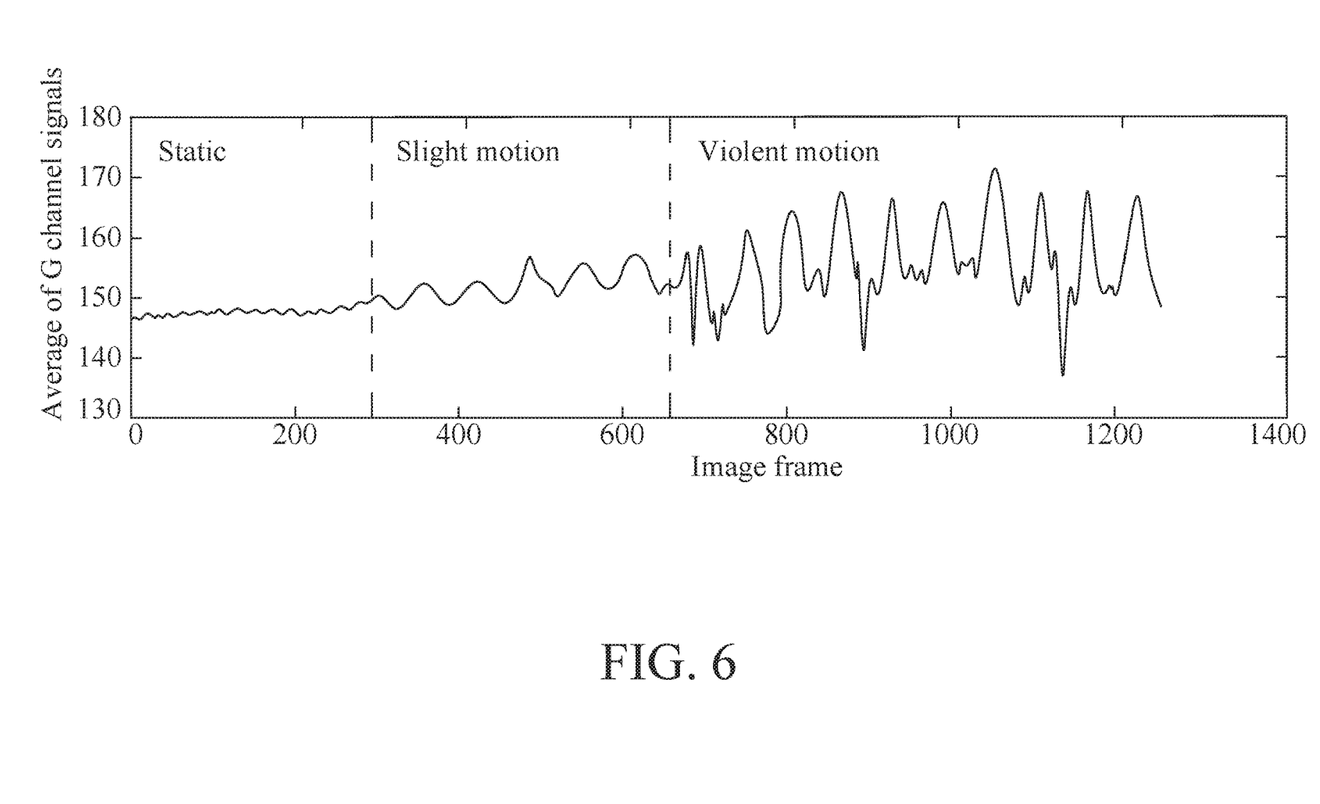
FIG. 6 is a chart showing a typical complexion fluctuation waveform obtained from calculating the arithmetic mean of green channel signals for an exemplary embodiment of the present invention.

FIG. 6 shows a typical complexion fluctuation waveform obtained from calculating the arithmetic mean of the green channel signals captured by the non-contact method, for determining the motion state in an exemplary embodiment of the present invention. In FIG. 6, the first segment in the horizontal axis correlates with the first waveform section corresponding to the static state, the second segment in the horizontal axis correlates with the second waveform section corresponding to the slightly motion state, and the third segment in the horizontal axis correlates with the third waveform section corresponding to the violent motion state. In the first waveform section corresponding to the static state, the heart-rate signal formed by the is hardly susceptible to noise interference so that the first waveform section is suitably applied to calculate corresponding heartbeat value as disclosed in step S170. Accordingly, only in the static state, the complexion fluctuation waveform is adopted by the operating unit to perform succeeding processes such as noise filtering disclosed in steps S140-S150, peak detecting disclosed in steps S160 and calculation of heartbeat value disclosed in steps S170. However, in the slightly motion state and the violent motion state, the corresponding second waveform section and third waveform section are only suitable for application of motion range detection as disclosed in step S130A instead for motion state detection as disclosed in step S130, and the operating unit does not take current waveform sections to process succeeding process(es) until next static state happens. Therefore, the method of the present invention not only reduces data or information to be processed in the succeeding processes such as noise filtering disclosed in steps S140-S150, peak detecting disclosed in steps S160 and calculation of heartbeat value disclosed in steps S170, but also improves the accuracy of detecting the heart-rate signal in the non-contact detection methodology.

As shown in FIG. 6, with alternative motion range detection as disclosed in step S130A of the detecting system in another exemplary embodiment of the present invention, the arithmetic means of channel signal for creating required complexion fluctuation waveform, which will be used in succeeding processes of motion range detection as disclosed in step S130A and peak detecting disclosed in steps S160 as well as calculation of disclosed in steps S170, is either arithmetic means of red channel signal or arithmetic means of blue channel signal.

In an algorithm for peak detecting process of steps S160, the time point of peak is identified that if corresponding slope or gradient of the complexion fluctuation waveform is analyzed in accordance with differential calculus such that a peak-to-peak time interval between any pair of adjacent peaks is calculated out via identifying the pair of adjacent peaks. Moreover, the heartbeat value disclosed in steps S170 is calculated in real time by determining the inverse number of the corresponding peak-to-peak time interval. Noticeably, a dynamic threshold is possibly added in the algorithm for peak detecting process to serve as a regulation means for ensuring the accuracy of the detecting result, wherein the n-th dynamic threshold ($T_n$) is defined as below:

$$T_n = C \times S_{n-1}$$

Wherein, all variables therein are defined as below: The C denotes a preset arbitrary coefficient in accordance with operation requirement, which is set in 0.35 for optimal detecting result; and the $S_{n-1}$ denotes a maximal slop value for preceding rising wave.

Moreover, with the dynamic threshold added in the detecting system of the exemplary embodiment, the dynamic threshold should be adjusted to follow with the variation of the complexion signals, and the detected slope thereof should be greater than the adjusted dynamic threshold for being defined as a peak possibly.

Figure 7:
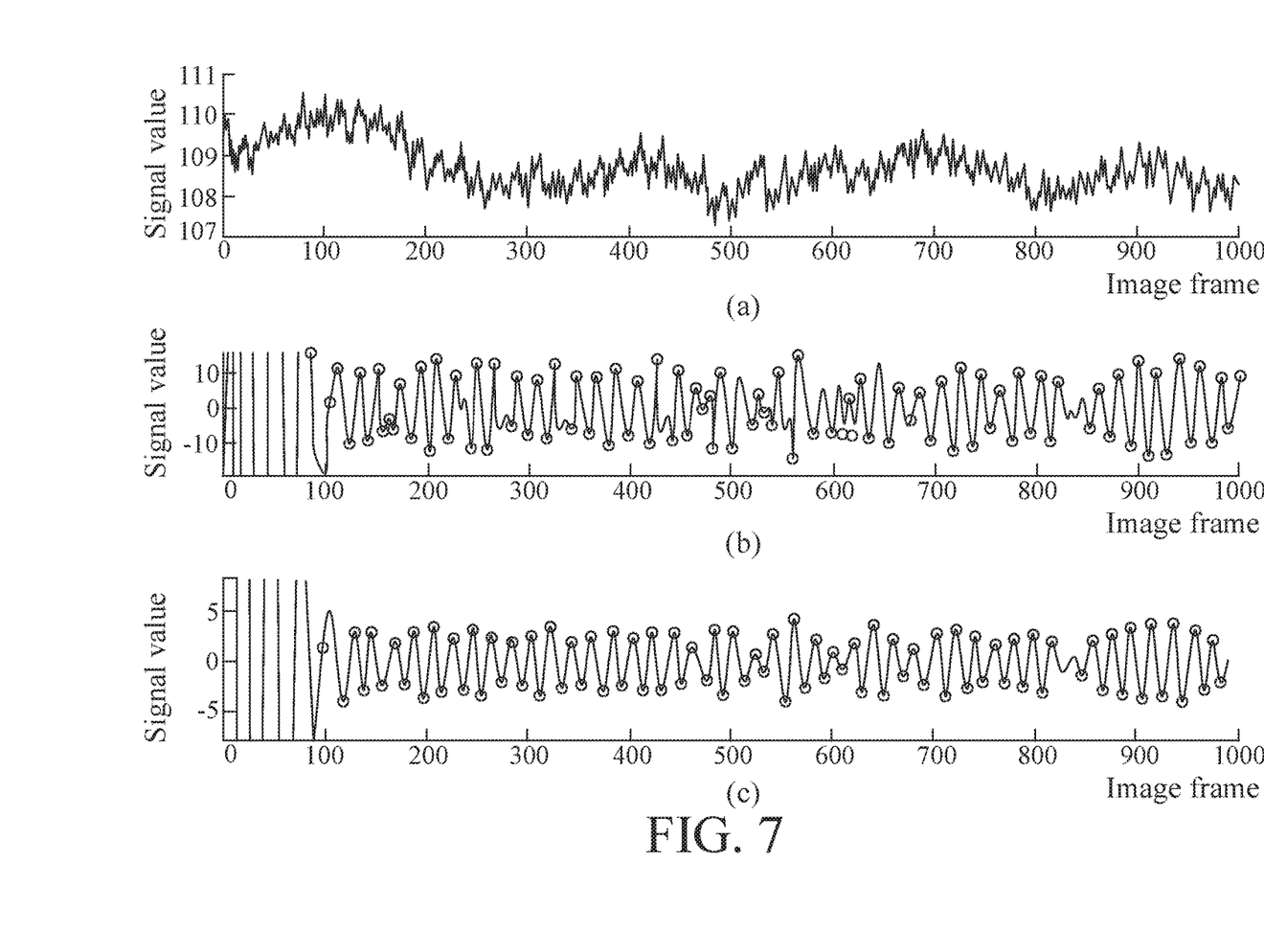
FIG. 7 includes three charts showing respective detected complexion signal with peak positions and peak values for an exemplary embodiment of the present invention as following: chart (a) shows the complexion signal that is initially captured by the optical sensing element; chart (b) shows the complexion signal that is subsequently filtered by the infinite impulse response filter; and chart (c) shows the complexion signal that is finally processed by the algorithm of moving average.

In FIGS. 7, (a), (b) and (c) are three charts showing respective detected complexion signal with peak positions and peak values for an exemplary embodiment of the present invention as following: (a) chart is a complexion signal that is captured by the optical sensing element; (b) chart is a complexion signal with the peak position that is detected after having been previously filtered by the infinite impulse response (IIR); and (c) chart is a final complexion signal with the peak position that is detected after having been previously processed by the algorithm of moving average. Analyzing FIGS. 7a, 7b and 7c, the inference is apparently derived as below. The complexion signal in (a) chart is unrefined with much noise. The complexion signal in (b) chart is preliminarily refined with the minor noise caused by slight variation due to non-heartbeat factors, and forms a preliminary waveform caused by variation of the heart rate; and the complexion signal in (c) chart is meticulously refined by attenuating or even completely removing the minor noise caused by slight variation due to non-heartbeat factors, so as to improve the accuracy of the peak detection.

Ultimately, in order to wirelessly transmit the final physiological signal(s) calculated from foregoing processes to other relevant smart device(s), following two succeeding processes are performed in serial order. The final physiological signal(s) can be transmitted via a Universal Asynchronous Receiver/Transmitter (UART) to a Bluetooth module (in step S600), then with Bluetooth module the final physiological signal(s) is converted into wireless output physiological signal(s) (in step S700) so that other relevant smart device(s) can effectively relay it/them to display on the phone interface related by mean of a waveform mode so that the remote monitoring effect is successfully achieved.

The foregoing descriptions of the preferred embodiments of the present invention have been presented for purposes of illustration and explanations. It is not intended to be exclusive or to limit the invention to the precise form or to the disclosed exemplary embodiments. Accordingly, the foregoing description should be regarded as illustrative rather than restrictive. Obviously, many modifications and variations will be apparent to practitioners skilled in this art. The embodiments are chosen and described in order to best explain the principles of the invention and its best mode for practical applications, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like is not necessary to confine the scope defined by the claims to a specific embodiment, and the reference to particularly preferred exemplary embodiments of the invention does not imply a limitation on the invention, and no such limitation is to be inferred. The invention is limited only by the spirit and scope of the appended claims. The abstract of the disclosure is provided to comply with the rules on the requirement of an abstract for the purpose of conducting survey on patent documents, and should not be used to interpret or limit the scope or meaning of the claims. Any advantages and benefits described hereto may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A non-contact method for detecting physiological signal and motion in real time, comprising steps of:
sensing a portion of a human body to generate a first image frame and a second image frame by an optical sensing element, wherein the second image frame is generated later than the first image frame;
providing a complexion judging mechanism by an operating unit for determining a first complexion region from the first image frame, and calculating a first central coordinate of the first complexion region;
the operating unit determining a first sampling block by acquiring a specific surrounding range expanded with the first central coordinate as an expanding center;
the operating unit determining a second complexion region from the second image frame by executing the complexion judging mechanism, and calculating a second central coordinate of the second complexion region;
determining a second sampling block by acquiring another specific surrounding range expanded with the second central coordinate as another expanding center;
the operating unit comparing the first central coordinate with the second central coordinate, to calculate a displacement in a unit time;
the operating unit discriminating whether a motion state of the portion of the human body is in a static state according to the displacement;
the operating unit calculating a physiological signal formed as a complexion fluctuation waveform in accordance with a complexion fluctuation between the first sampling block and the second sampling block if the motion state of the portion of the human body is in the static state; and
transmitting the physiological signal to a relevant receiving device.

2. The non-contact method for detecting physiological signal and motion in real time as claimed in the claim 1, further comprising:
the operating unit calculating an area of the first complexion region;
judging whether the area of the first complexion region is larger than a preset area or not;
displaying the first sampling block in a succeeding image frame following the first image frame on a display unit, and the operating unit determining the portion of the human body is really sensed by the optical sensing element if the area of the first complexion region is larger than a preset area threshold; and
the operating unit generating and sending a warning signal to the relevant receiving device to alert a user if the area of the first complexion region is smaller than the preset area threshold.

3. The non-contact method for detecting physiological signal and motion in real time as claimed in the claim 2, further comprising:
determining the portion of the human body is not really sensed by the optical sensing element, and generating an alerting signal by an alarm unit if the area of the first complexion region is less than the preset area threshold.

4. The non-contact method for detecting physiological signal and motion in real time as claimed in the claim 1, further comprising: the operating unit executing a motion detecting mechanism comprising steps of:
receiving a first displacement critical value and a second displacement critical value preset by the user, wherein the first displacement critical value is less than the second displacement critical value;
the operating unit retrieving the first displacement critical value and the second displacement critical value to respectively compare with the displacement;
if the displacement is not greater than the first displacement critical value, then the operating unit defining the portion of the human body is in a static state;
if the displacement is greater than the first displacement critical value and not greater than the second displacement critical value, then defining the portion of the human body is in a slightly motion state;
if the displacement is greater than the second displacement critical value, then defining the portion of the human body is in a violent motion state; and
changing the first displacement critical value and the second displacement critical value by the operating unit, to adjust a sensitivity of the motion detecting mechanism.

5. The non-contact method for detecting physiological signal and motion in real time as claimed in the claim 1, wherein each of the first image frame and the second image frame includes a plurality of pixels, the operating unit executes the complexion judging mechanism to judge that each of the pixels is a skin-color pixel or a nonskin-color pixel, wherein the complexion judging mechanism comprises steps of:

selecting one of the pixels to be a central pixel, and defining a judging block by outspreading from the central pixel to the surrounding thereof;

calculate an area ratio of a skin-color area located in the judging block to an entire area of the judging block, wherein the skin-color area is formed by the skin-color pixels in the judging block and located around the central pixel;

the operating unit receiving a reference ratio preset by the user, and comparing the area ratio with the reference ratio; and determining the central pixel is a nonskin-color pixel if the area ratio is less than the reference ratio.

6. The non-contact method for detecting physiological signal and motion in real time as claimed in the claim 1, further comprising: the operating unit calculating one of an average of red channel signals, an average of green channel signals and an average of blue channel signals for each of the first sampling block and the second sampling block, to create the complexion fluctuation waveform.

7. The non-contact method for detecting physiological signal and motion in real time as claimed in the claim 6, further comprising:

obtaining a real ambient illuminance via the optical sensing element;

the operating unit receiving an illuminance threshold preset by the user, and comparing the real ambient illuminance with the illuminance threshold by the operating unit, so as to obtain a comparing result;

preparing a light source of infra-red, and selecting one of a switch-on mode and a switch-off mode for the light source of infra-red in accordance with the comparing result;

switching the light source of infra-red into the switch-off mode and using the average of green channel signals for creating the complexion fluctuation waveform if the real ambient illuminance is greater than the illuminance threshold as the comparing result; and switching the light source of infra-red into the switch-on mode and using the average of red channel signals for creating the complexion fluctuation waveform if the real ambient illuminance is less than the illuminance threshold as the comparing result.

8. The non-contact method for detecting physiological signal and motion in real time as claimed in the claim 1, further comprising: inputting the physiological signal into an infinite impulse response filter to perform filtering process for generating an output signal.

9. The non-contact method for detecting physiological signal and motion in real time as claimed in the claim 8, further comprising:

providing a moving average algorithm for the operating unit;

the operating unit executing the moving average algorithm to smooth a waveform of the output signal generated from the infinite impulse response filter.

10. The non-contact method for detecting physiological signal and motion in real time as claimed in the claim 1, wherein the operating unit is a field-programmable gate array with an internal microprocessor, the field-programmable gate array executes the complexion judging mechanism, and the internal microprocessor calculates the physiological signal.

\* \* \* \* \*